(12) United States Patent
Dede et al.

(10) Patent No.: US 12,064,708 B2
(45) Date of Patent: Aug. 20, 2024

(54) SYSTEMS AND METHODS FOR ADDITIVE MANUFACTURING OF WICK STRUCTURE FOR VAPOR CHAMBER

(71) Applicant: TOYOTA MOTOR ENGINEERING & MANUFACTURING NORTH AMERICA, INC., Erlanger, KY (US)

(72) Inventors: Ercan Dede, Ann Arbor, MI (US); Feng Zhou, South Lyon, MI (US); Shailesh N. Joshi, Ann Arbor, MI (US)

(73) Assignee: TOYOTA MOTOR ENGINEERING & MANUFACTURING NORTH AMERICA, INC., Erlanger, KY (US)

( * ) Notice: Subject to any disclaimer, the term of this patent is extended or adjusted under 35 U.S.C. 154(b) by 838 days.

(21) Appl. No.: 17/164,547

(22) Filed: Feb. 1, 2021

(65) Prior Publication Data
US 2021/0161029 A1    May 27, 2021

Related U.S. Application Data

(62) Division of application No. 15/699,549, filed on Sep. 8, 2017, now abandoned.

(51) Int. Cl.
*B01B 1/00* (2006.01)
*B22F 3/11* (2006.01)
(Continued)

(52) U.S. Cl.
CPC ............ *B01B 1/005* (2013.01); *B22F 3/1121* (2013.01); *B22F 5/10* (2013.01); *B22F 7/002* (2013.01);
(Continued)

(58) Field of Classification Search
CPC .......... B01B 1/005; B22F 3/1121; B22F 5/10; B22F 7/002; B22F 7/004; B22F 7/08; B22F 10/16; B22F 10/28; B22F 12/53; B22F 2999/00; B33Y 10/00; B33Y 80/00; H05K 7/20336; H05K 7/20381; A61L 2209/135; F28F 2255/18; G06F 2200/201; G06F 1/203; G06F 1/20; Y02P 10/25
See application file for complete search history.

(56) References Cited

U.S. PATENT DOCUMENTS

| 7,866,372 B2 | 1/2011 | Slaughter |
| 2007/0056712 A1 | 3/2007 | Yu |

(Continued)

*Primary Examiner* — Adil A. Siddiqui
(74) *Attorney, Agent, or Firm* — Oblon, McClelland, Maier & Neustadt, L.L.P.

(57) ABSTRACT

A vapor chamber includes a wick structure created by an additive selective laser sintering process. The wick structure includes a substrate, a first copper powder layer, a second copper powder layer, and a plurality of additional layers. The first copper powder layer is deposited across the substrate, wherein the first copper powder layer is subsequently selectively fused via a fusing instrument. The second copper powder layer is deposited across the first copper powder layer, wherein the second copper powder layer is subsequently selectively fused via the fusing instrument. Additionally, a plurality of additional copper powder layers are deposited wherein each additional layer is deposited on the previous layer, wherein each of the additional copper powder layers is selectively fused with a predetermined structure.

9 Claims, 9 Drawing Sheets

(51) Int. Cl.
*B22F 5/10* (2006.01)
*B22F 7/00* (2006.01)
*B22F 7/08* (2006.01)
*B22F 10/16* (2021.01)
*B22F 10/28* (2021.01)
*B22F 12/53* (2021.01)
*B33Y 10/00* (2015.01)
*B33Y 80/00* (2015.01)
*H05K 7/20* (2006.01)

(52) U.S. Cl.
CPC ............... *B22F 7/004* (2013.01); *B22F 7/08* (2013.01); *B22F 10/16* (2021.01); *B22F 10/28* (2021.01); *B33Y 10/00* (2014.12); *B33Y 80/00* (2014.12); *H05K 7/20336* (2013.01); *H05K 7/20381* (2013.01); *A61L 2209/135* (2013.01); *B22F 12/53* (2021.01); *B22F 2999/00* (2013.01); *F28F 2255/18* (2013.01); *G06F 2200/201* (2013.01)

(56) References Cited

U.S. PATENT DOCUMENTS

| | | |
|---|---|---|
| 2009/0321045 A1 | 12/2009 | Hernon |
| 2010/0065255 A1 | 3/2010 | Liu |
| 2012/0175086 A1 | 7/2012 | Rosenfel |
| 2013/0003303 A1 | 1/2013 | Lindgren |
| 2015/0246484 A1 | 9/2015 | Hirschberg |
| 2015/0289413 A1 | 10/2015 | Rush |
| 2015/0306664 A1* | 10/2015 | Åklint ................ A61C 13/0018 264/16 |
| 2016/0069622 A1 | 3/2016 | Alexiou |
| 2017/0064868 A1* | 3/2017 | Rush ................... F28D 15/0233 |
| 2017/0106113 A1 | 4/2017 | Meinhart |
| 2017/0108210 A1 | 4/2017 | Meinhart |
| 2017/0253982 A1 | 9/2017 | Kimble |
| 2017/0293329 A1 | 10/2017 | Chiriac |
| 2018/0120912 A1 | 5/2018 | Jenkins |
| 2019/0014688 A1* | 1/2019 | Weibel ................... B23P 15/26 |

* cited by examiner

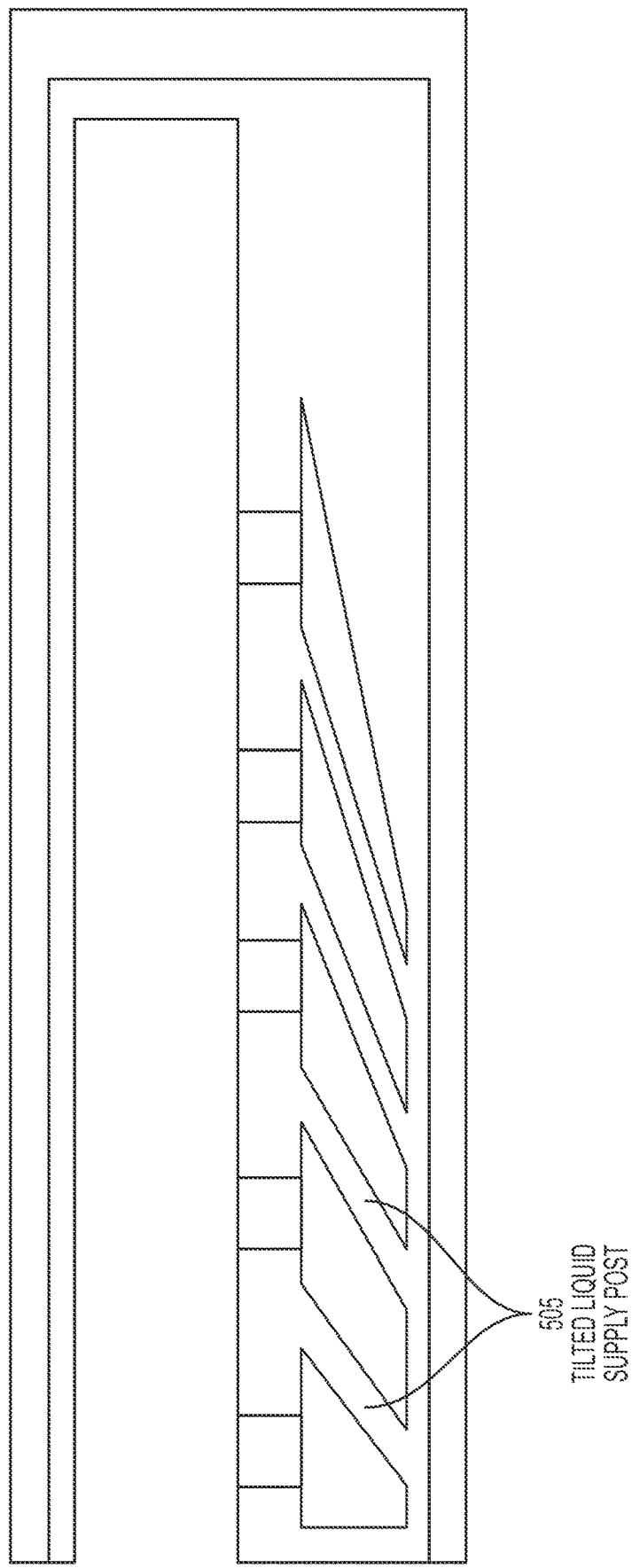

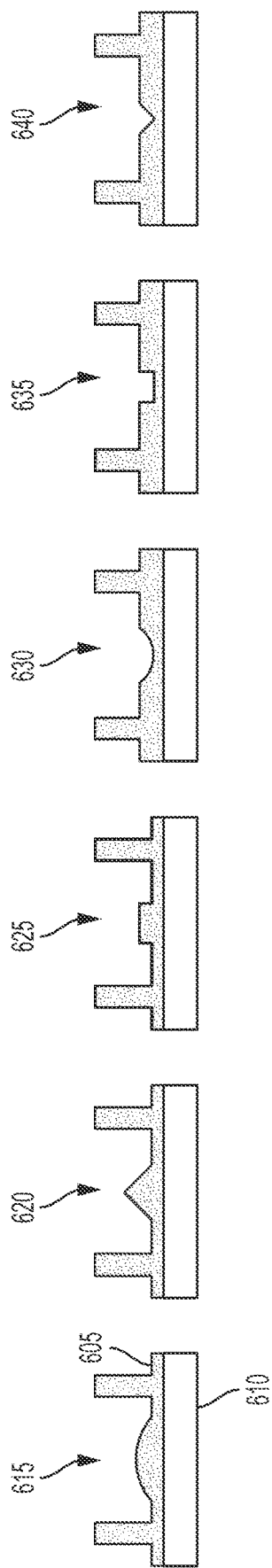
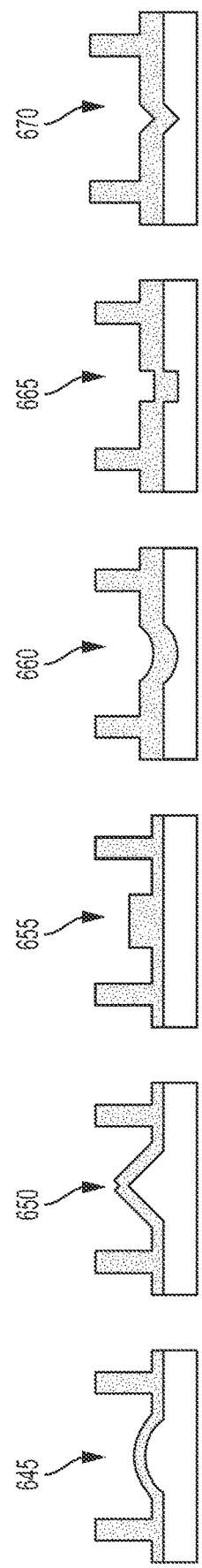
FIG. 6A
FIG. 6B

SYSTEMS AND METHODS FOR ADDITIVE MANUFACTURING OF WICK STRUCTURE FOR VAPOR CHAMBER

CROSS-REFERENCE TO RELATED APPLICATIONS

This application is a division of U.S. application Ser. No. 15/699,549 filed Sep. 8, 2017, the entire contents of which is incorporated herein by reference.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The intensifying electrification of transportation systems and clean-energy-production technologies has dramatically increased the waste heat load that must be dissipated from high-density power electronic devices. This trend has pushed conventional air-cooling thermal management architectures to the limit. A reliance on conduction heat spreading from devices to the heat rejection surfaces incurs an overly large thermal resistance at power levels well below the inherent electrical power density limits of devices.

Vapor chamber heat spreaders offer a viable solution if implemented as a heat sink base, unlike alternative solid heat conduction spreaders that are fundamentally limited to a linearly decreasing performance (increasing thermal resistance) with effective heat transfer distance. A sealed vapor chamber can be filled with a working fluid that evaporates when locally heated. The vapor flows away from the hotspot and condenses over a diffuse heat rejection surface. A porous wick structure lining the chamber pumps liquid back to the heat sources via capillary action. This two-phase cycle allows passive heat spreading at a temperature gradient that can be orders of magnitude lower than conduction through solid materials. Vapor chambers have high reliability, passive operation, and effective heat transport.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

According to embodiments of the disclosed subject matter, a vapor chamber includes a wick structure created by an additive selective laser sintering process. The wick structure includes a substrate, a first copper powder layer, a second copper powder layer, and a plurality of additional layers. The first copper powder layer is deposited across the substrate, wherein the first copper powder layer is subsequently selectively fused via a fusing instrument. The second copper powder layer is deposited across the first copper powder layer, wherein the second copper powder layer is subsequently selectively fused via the fusing instrument. Additionally, a plurality of additional copper powder layers are deposited wherein each additional layer is deposited on the previous layer, wherein each of the additional copper powder layers is selectively fused with a predetermined structure.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5 depicts tilted liquid supply posts according to one or more aspects of the disclosed subject matter;

FIG. 6A depicts exemplary surface enhancements with a flat substrate according to one or more aspects of the disclosed subject matter;

FIG. 6B depicts exemplary surface enhancements with a featured substrate according to one or more aspects of the disclosed subject matter;

DETAILED DESCRIPTION

Figures 1A, 1B:
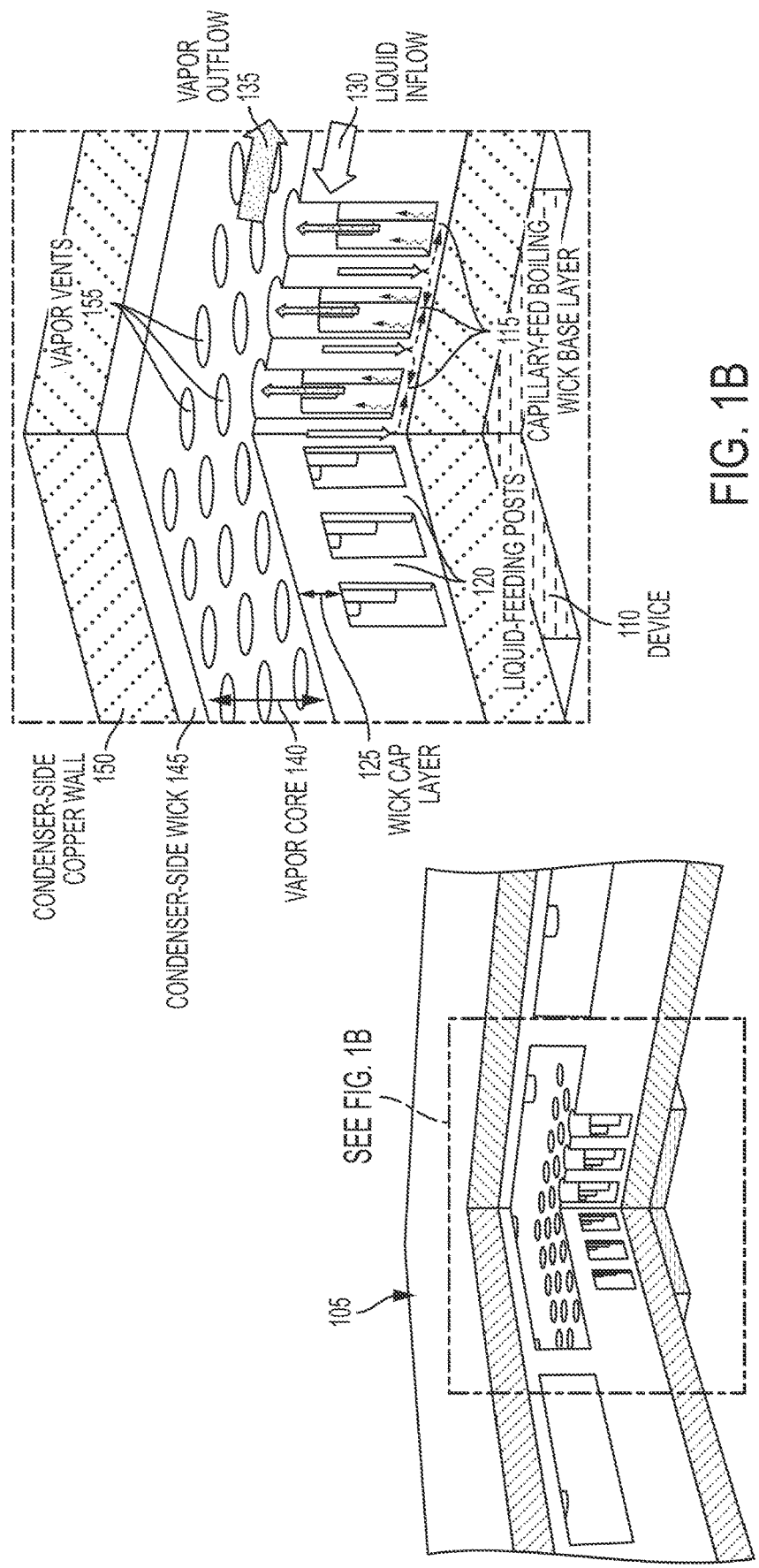
FIG. 1A depicts an exemplary overview of a vapor chamber according to one or more aspects of the disclosed subject matter.
FIG. 1B depicts a detailed view of a portion of a vapor chamber according to one or more aspects of the disclosed subject matter.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one embodiment" or "an embodiment" means that a particular feature, structure, characteristic, operation, or function described in connection with an embodiment is included in at least one embodiment of the disclosed subject matter. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments. Further, it is intended that embodiments of the disclosed subject matter can and do cover modifications and variations of the described embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the disclosed subject matter to any particular orientation or configuration. Furthermore, terms such as "first," "second," "third," etc., merely identify one of a number of portions, components, points of reference, operations and/or functions as described herein, and likewise do not necessarily limit embodiments of the disclosed subject matter to any particular configuration or orientation.

Referring now to the drawings, wherein like reference numerals designate identical or corresponding parts throughout the several views.

FIGS. 1A-1B depicts an exemplary overview of a vapor chamber 105 according to one or more aspects of the disclosed subject matter. FIGS. 1A-1B depicts a detailed view of a portion of a vapor chamber according to one or more aspects of the disclosed subject matter. The vapor chamber 105 may be used to cool a device 110, wherein the device 110 may be a CPU, a graphics card, and the like, for example. The vapor chamber 105 may include a capillary-fed boiling wick base layer 115, one or more liquid-feeding posts 120, a wick cap layer 125, liquid inflow 130, vapor outflow 135, vapor core 140, a condenser-side wick 145, a condenser-side copper wall 150, and one or more vapor vents 155. The vapor chamber 105 can be an example of a typical vapor chamber and one or more components of the vapor chamber 105 may be modified and/or removed. Additionally, new components may be added and new processes for creating one or more components may be used as further described herein. Further, one or more components of the vapor chamber 105 may simply be used for reference when describing aspects of the disclosed subject matter.

Figure 2A:
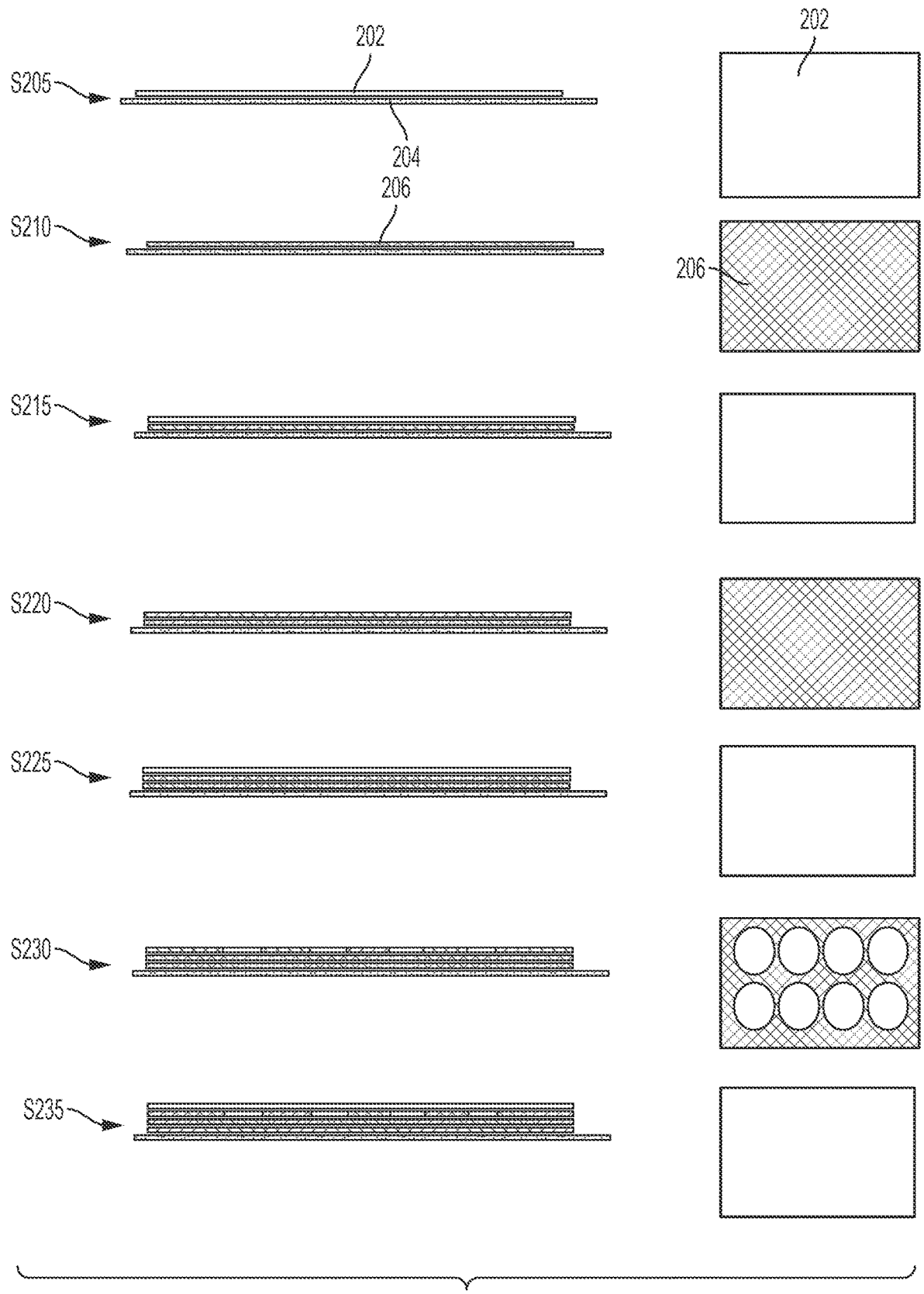
FIG. 2A depicts exemplary steps in an additive layer fabrication process for a multi-layer wick structure according to one or more aspects of the disclosed subject matter.
Figure 2B:
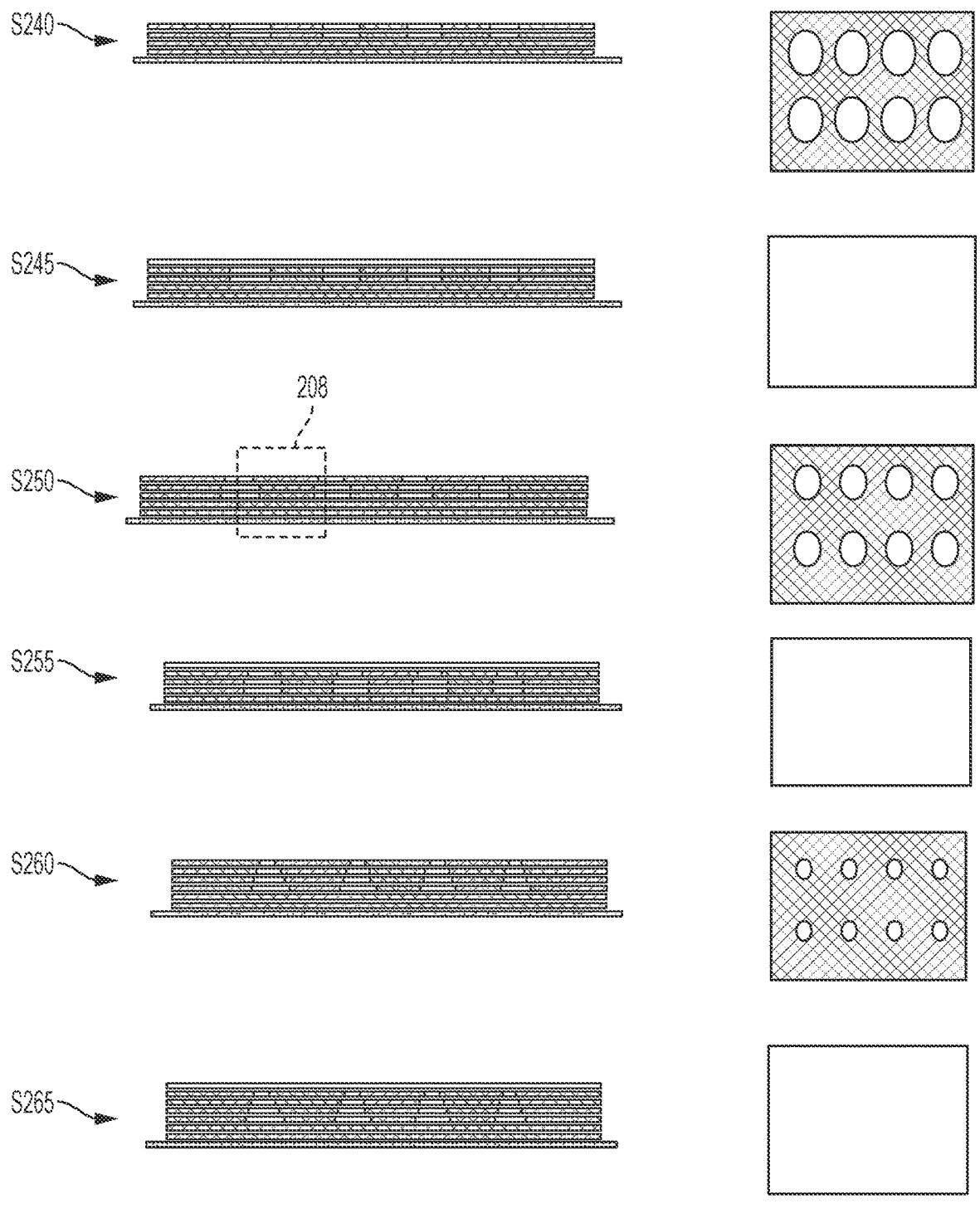
FIG. 2B depicts exemplary steps in an additive layer fabrication process for a multi-layer wick structure according to one or more aspects of the disclosed subject matter.
Figure 2C:
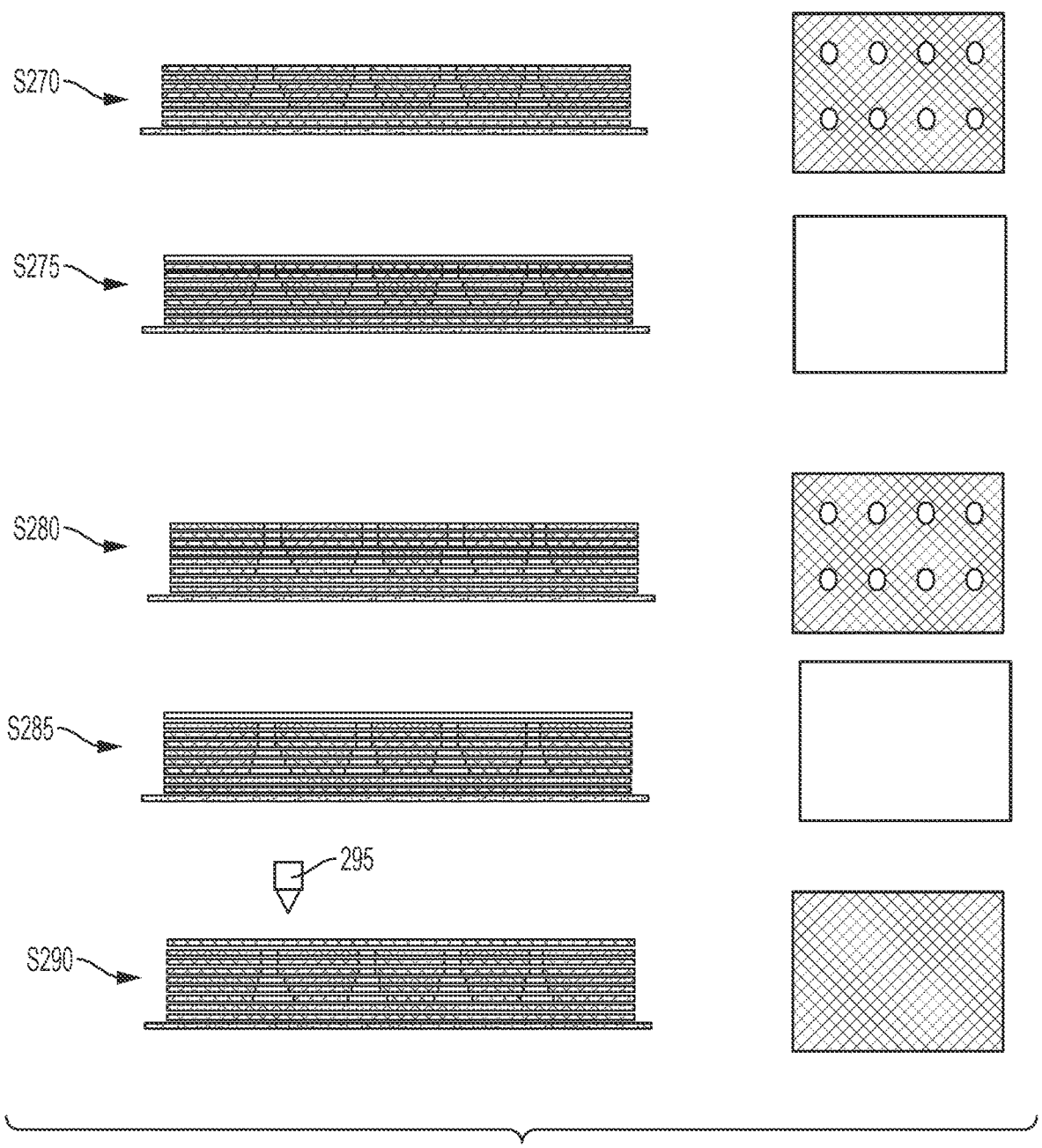
FIG. 2C depicts exemplary steps in an additive layer fabrication process for a multi-layer wick structure according to one or more aspects of the disclosed subject matter.

FIG. 2A-FIG. 2C depicts an additive layer fabrication process for the multi-layer wick structure. The additive layer fabrication process is advantageous in that it can solve a wick degradation issue from laser etching. Additionally, the process can enable the integration of surface features or micro-structures not easily attainable from molding or subtractive fabrication methods. For example, arch structures and other unique structures may now be included during manufacturing which would not be possible through a subtractive process. The arch structures may reduce a pressure drop of cooling fluid returning to the base wick layer from a condensing layer, for example.

An advantage of fabricating the porous multi-wick structure of a vapor chamber using an additive manufacturing process is that numerous designs may be manufactured without the need for new tooling or implementation of damaging subtractive manufacturing processes such as laser etching or machining.

In general, one embodiment of an additive manufacturing process may include starting with a first copper powder layer (S205) which is selectively fused/sintered by a laser (S210). In an embodiment, any copper power layer can be a copper alloy powder layer, for example. A second copper powder layer may be added on top of the selectively fused first copper powder layer (S215) and a laser may again selectively fuse portions of the second copper powder layer (S220). The cycle of adding layers of copper powder and selectively fusing portions of the copper powder may be repeated until the porous multi-layer wick structure is formed. The loose copper powder that remains may be removed in a post-processing step, for example.

In an embodiment, once the copper powder in the previously applied layer is fused the loose/unfused copper powder may be removed (e.g., by compressed air) and replaced with sacrificial carbonate particles to provide support for the subsequent layers of copper powder. The sacrificial carbonate particles may include a binding agent that is curable between applications to prevent the binding agent from being removed during subsequent applications of copper powder layers. Once the multi-layer wick structure is constructed, the sacrificial carbonate particles may be sintered out through a loose sintering process which may additionally sinter the copper particle preform into a final porous multi-layer wick structure.

In an embodiment, a copper powder suspended in a slurry with a binding agent (e.g., polymeric) may be prepared. The slurry may be applied to a substrate in layers via an applicator nozzle (e.g., print nozzle 295 in FIG. 2C) preprogrammed with the porous multi-layer wick structure. The print nozzle 295 and/or a machine controlling the print nozzle 295 can include a memory to store instructions and predetermined wick structures, for example, and a processor to perform the steps for creating the predetermined wick structure. The binding agent may be partially cured as each layer is applied to form a 3-dimensional construct of the porous multi-layer wick structure. The construct may then be sintered such that the copper powder forms a porous structure and the binding agent is removed.

In an embodiment, an ultrasonic bonding process may be utilized to initially bond portions of copper powder or copper power slurry constructs during an additive layering process. The ultrasonically bonded copper powder may finally be formed through a subsequent ultrasonic process or a sintering process, for example.

More specifically, FIG. 2A-2C includes an example step-by-step process flow of an additive selective laser sintering process. Each step includes a cross-sectional view and top view for reference. As noted above, variations to the general additive layer manufacturing process may be utilized in achieving the desired porous multi-layer wick structure.

In S205, copper powder 202 can be deposited across a support surface 204. The support surface 204 may be a copper plate, a mold, or any other surface for supporting the additive manufacturing of the multi-layer wick structure.

In S210, laser (e.g., or a similar fusing instrument) can be used to selectively fuse the copper powder (e.g., fused copper powder 206).

Once the copper powder is fused, another layer of copper powder may be added to the fused layer in S215 and subsequently selectively fused with a laser or similar fusing instrument (e.g., the entire build platform may be positioned in an oven) in S220.

Similarly, S225, S230, S235, S240, S245, and S250 show the addition of additional copper powder layers and the subsequent selective fusing (e.g., laser, oven, etc.). The selectively fused copper powder is shown by way of dark grey and free or loose copper powder is shown as light grey. Additionally, the formation of liquid supply posts 208 is depicted wherein the liquid supply posts include an arch structure. The arch structure may provide additional structural support to the multi-wick layer as well as improved cooling of vapor.

Further, S255, S260, S265, S270, S275, S280, S285, and S290 continue the build-up of the multi-layer wick structure through the continued addition of copper powder and selective fusing of the copper powder (e.g., via a laser or oven). S290 also depicts an exemplary print nozzle 295 that may be part of an additive manufacturing machine, for example. The print nozzle 295 may be used in the additive manufacturing process to apply a slurry to a substrate in layers wherein the print nozzle may be preprogrammed with the porous multi-layer wick structure.

It should be appreciated that the process described in FIGS. 2A-2C is an example of a design and one example additive layer manufacturing process. The multi-layer wick structure may further be assembled with a vapor chamber housing and cooling fluid. The completed vapor chamber may be coupled to a heat source such as an electronics package for purposes of removing heat generated by the electronics package.

The additive method of fabrication can avoid the issues created by laser etching sintered wick structures to remove material. Further, surface enhancement features, arch structures, and other unique features may be formed without the need for specialized molds or subtractive processes.

In an embodiment, each layer in S205 through S290 can be printed (e.g., via a 3D printer) at room temperature, where the polymeric binder produces a geometrically (i.e., gravity) stable part including the metal particles. The fusing or sintering of the metal particles may be done in a single post-printing step where the polymeric binder can be burned off, for example.

Further considerations may include adjusting laser sintering temperatures for forming porous wick structures versus forming a solid metal structure. Additionally, unique binding agents (e.g. chemical binders or physical (e.g. polymeric) binders) may be used. Further, intermediate heating or cooling steps to control porosity of the multi-layer wick may be used.

Figure 3A:
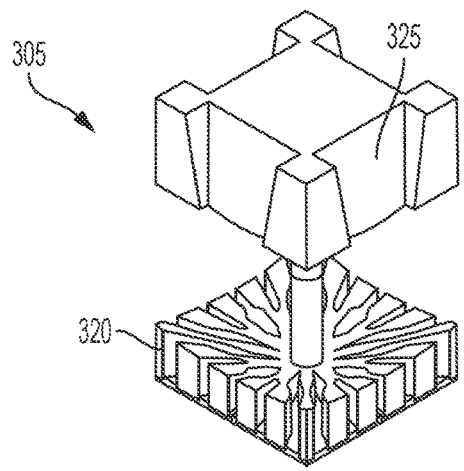
FIG. 3A depicts a wick unit cell from an optimized wick structure according to one or more aspects of the disclosed subject matter.

FIG. 3A depicts a wick unit cell 305 from an optimized wick structure according to one or more aspects of the disclosed subject matter. The wick unit cell 305 can include an arched liquid feeding post 315 (e.g., seen more clearly in FIG. 3B), a structured based wick 320 with non-uniform height (e.g., thicker further from liquid feeding post), and a tapered outlet vent 325, for example.

Figure 3B:
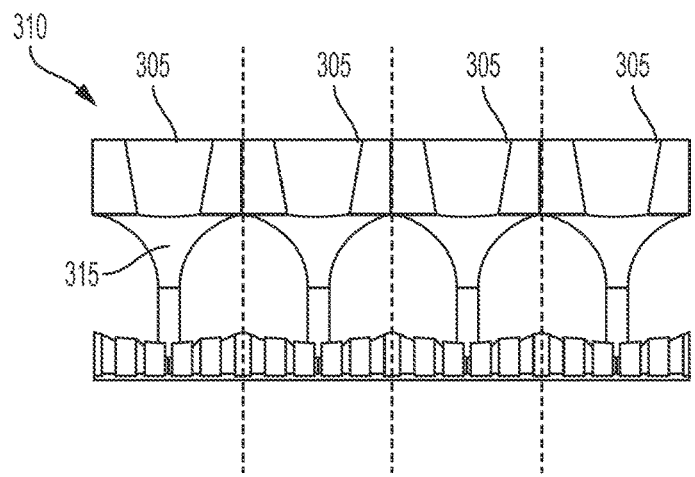
FIG. 3B depicts a side view of an optimized wick structure according to one or more aspects of the disclosed subject matter.

FIG. 3B depicts a side view of the optimized wick structure 310 according to one or more aspects of the disclosed subject matter. The optimized wick structure 310 may include a plurality of wick unit cells 305, for example. The wick cell units 305 can be connected via sintering together the wick cell units 305, for example.

Figure 3C:
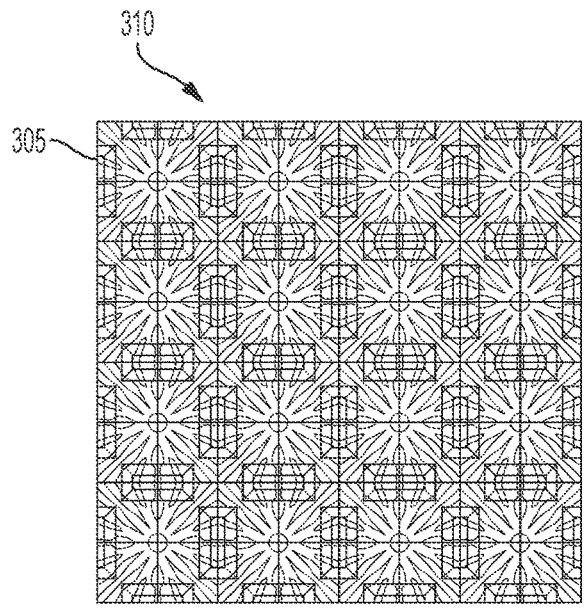
FIG. 3C depicts a top view of an optimized wick structure according to one or more aspects of the disclosed subject matter.

FIG. 3C depicts a top view of the optimized wick structure 310 according to one or more aspects of the disclosed subject matter. An advantage of the optimized wick structure 310 can optimize the vapor flow path. In other words, the vapor can flow to the condenser side and the liquid can flow to the evaporator side as efficiently as possible. In an embodiment, the liquid feeding posts 120 in FIG. 1 can include the optimized wick structure 310, for example.

Figure 4:
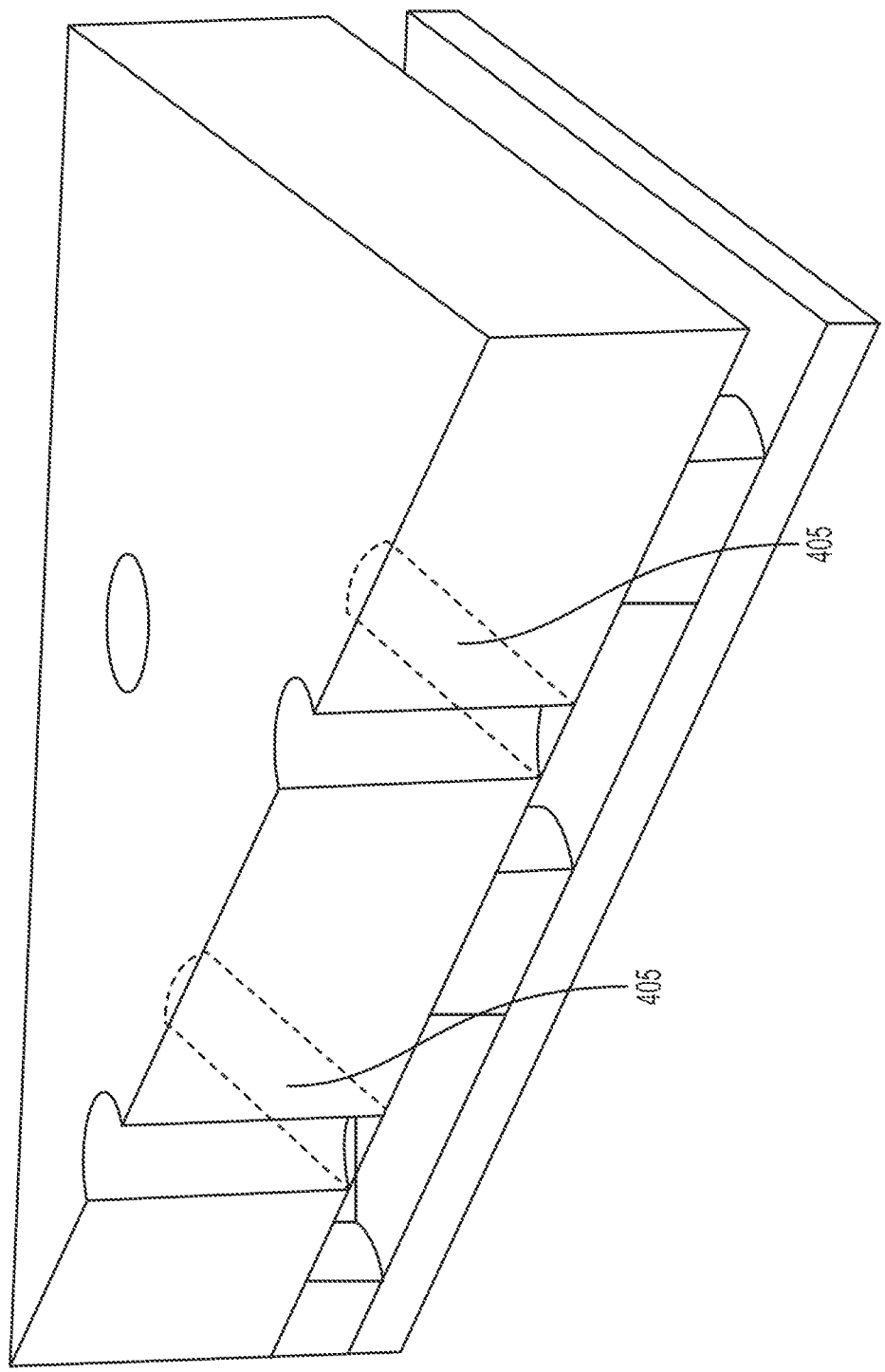
FIG. 4 depicts vapor vents angled towards the periphery of a vapor chamber according to one or more aspects of the disclosed subject matter.

FIG. 4 depicts vapor vents 405 angled towards the periphery of the vapor chamber (e.g., vapor chamber 105) according to one or more aspects of the disclosed subject matter. In a typical vapor chamber, only a center region has two layer wick structure and vapor can only flow out through vapor vents. The center region of the condenser side may have vapor flow impinged on it, leading to non-uniform condensation heat transfer on condenser side and also potential erosion. However, constructing angled vapor vents 405 (e.g., via 3D printing) angled towards the periphery of the vapor chamber can better distribute the vapor flow towards the condenser side, cause less impact to the condenser wick, and provide more uniform condensation heat transfer.

FIG. 5 depicts tilted liquid supply posts 505 according to one or more aspects of the disclosed subject matter. Each titled liquid supply post 505 can be titled at a more severe angle closer to the periphery of the vapor chamber. Typically, the area that has vapor vents can be the same as the area of heat source. Because the volume of vapor is about 1000 times that of liquid, a larger area for vapor flow can be advantageous. Accordingly, the titled liquid supply posts 505 can provide a larger area for vapor flow compared to heat source area. Tilted liquid supply posts 505 can connect larger vapor vent area and smaller heated area. The titled liquid supply posts can be advantageous for a vapor chamber with multiple heat sources with different heat flux levels, for example. In an embodiment, the tilted liquid supply posts 505 can be combined with the angled vapor vents 405 shown in FIG. 4.

FIG. 6A depicts exemplary surface enhancements with a flat substrate according to one or more aspects of the disclosed subject matter, and FIG. 6B depicts exemplary surface enhancements with a featured substrate according to one or more aspects of the disclosed subject matter. Each surface enhancement example can include a base wick 605 and a substrate 610, as shown in surface enhancement example 615, for example. The surface enhancement features can be added to the base wick 605 only or added to both base wick 605 and the substrate 610, for example. Additionally, the surface enhancement features can be constructed via additive manufacturing, for example. The surface enhancement feature can be dimples (e.g., 630, 635, 640, 660, 665, and 670) or bumps (e.g., 615, 620, 625, 645, 650, and 655). The shapes of dimple and bump can also be pyramid (e.g., 620 and 650), elliptical dimple (e.g., 615, 645, 630, and 660), rectangular (e.g., 625, 655, 635, and 665), diamond (e.g., 640 and 670), and the like. Any shape of dimples or bumps can be applicable. When the substrate has the similar shape of dimples or bumps as the base wick, more uniform heat flux can be provided to the surface enhancement features. The geometries of the surface enhancing features are further describe in provisional application 62/469,784 filed on Mar. 10, 2017, which is herein incorporated by reference in its entirety.

Figure 7B:
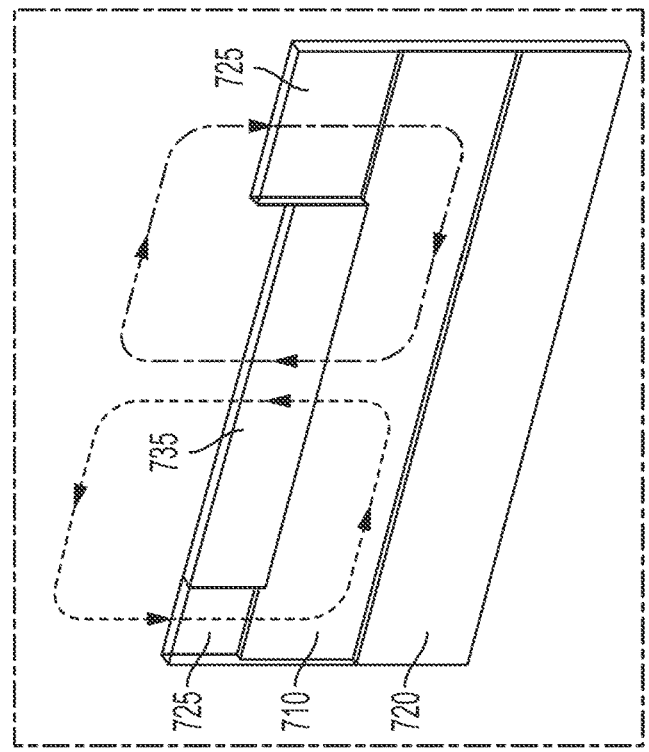
FIG. 7B depicts a close up view of a portion of a manifold microchannel wick structure according to one or more aspects of the disclosed subject matter.
Figure 7A:
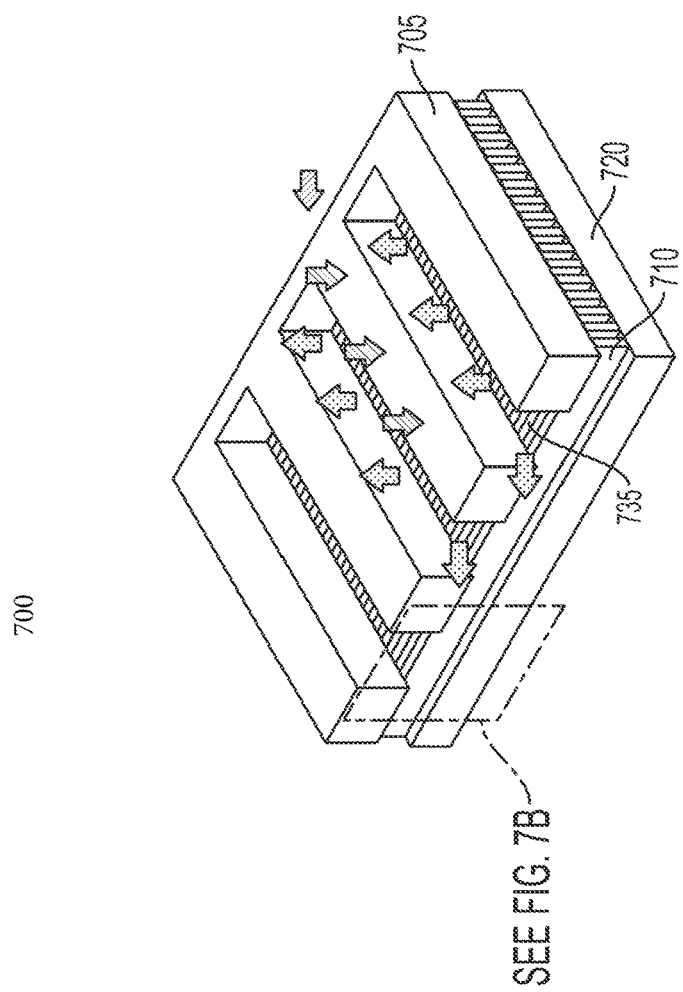
FIG. 7A depicts a manifold microchannel wick structure according to one or more aspects of the disclosed subject matter.

FIG. 7A depicts a manifold microchannel wick structure 700 as a schematic of a manifold microchannel heat sink according to one or more aspects of the disclosed subject matter. The manifold microchannel wick structure 700 can be applied to a vapor chamber, for example, and can be constructed via additive manufacturing. The manifold microchannel wick structure 700 can include a manifold 705 and microchannels 710, wherein the manifold 705 and the microchannels 710 can be made of a porous wick structure.

The microchannels 710 can be on an evaporator side corresponding to evaporator 720. FIG. 7B depicts a close up view of a portion of the manifold microchannel wick structure 700 according to one or more aspects of the disclosed subject matter. FIG. 7B depicts a vapor flow cycle (e.g., vapor to liquid cycle) wherein the vapor may rise from the microchannels 710 through gaps between fingers of the manifold 705 as depicted by the arrows pointing up and away from the microchannels 710. Additionally, FIG. 7B more specifically shows the portions 725 of the manifold, which can be a porous wick structure. The portions 725 assist in returning liquid, e.g., after the vapor rising between the gaps between the fingers of the manifold 705 reaches the condenser (not shown) to the evaporator 720 as indicated by the arrows point down toward the manifold 705, for example. Although the shape of portions 725 are square, the shape of portions 725 can include various geometries based on the construction of the manifold 705, for example, via additive manufacture. Additionally, portion 735 can correspond to a gap between the fingers of the manifold 705, for example. More specifically, the vapor can flow through the open area corresponding to portion 735 on its way toward the condenser, for example. An advantage of using additive manufacturing is to create geometries that are not easily machined, or possibly cannot be machined. Additionally, the manifold microchannel wick structure 700 can include wider channels on a condenser side (e.g., a side of the manifold opposite the evaporator side) and narrow channels on an evaporator side 720. For example, based on a heat capacity and desired vapor flow configuration, the channels can be wider, narrower, increase a number of channels, decrease a number of channels, and the like. All channel walls (e.g., manifold 705, portions 725, microchannels 710, etc.) can be made of porous wick, for example. The channel walls can function as a liquid supply route, and the space between the channel walls can be for vapor flow.

The channel walls on the manifold 705 can enhance the liquid return from condenser side to evaporator side. This can be advantageous because in a traditional vapor chamber, liquid only returns through the wick on the side wall of the chamber. Additionally, denser channel walls on the evaporator side can help with getting the local liquid supply to a hot spot. The density can vary based on the heat flux level, for example. Further, the profile of the channels looking from the side can be sinusoidal, square, triangle, sawtooth, and the like. An advantage of having alternative channel profiles can minimize the vapor flow resistance and/or obstruction to vapor flow and allow better liquid flow. The channel profile can be selected based on an application of the heat sink, the heat flux requirement for the application, and the like.

Aspects of the disclosed subject matter include several advantages. For example, manufacturing a porous multi-layer wick structure for a vapor chamber using an additive manufacturing method does not require specialized molding tools or subtractive material processes that can be damaging to the wick and/or wick structure. Additionally, fabricating the porous multi-wick structure of a vapor chamber using an additive manufacturing process can include numerous designs that can be manufactured without the need for new tooling.

Additionally, several structural advantages can be provided via the optimized wick structure, the angled vapor vents, the titled liquid supply posts, the surface enhancements, the manifold microchannel wick structure, and the like to improve various aspects of cooling in a vapor chamber including dealing with multiple heat sources with different heat flux levels, for example. It should be appreciated that one or more of the embodiments described herein can be combined in a vapor chamber.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numerous modifications and other embodiments (e.g., combinations, rearrangements, etc.) are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

The invention claimed is:

1. A method for additive selective laser sintering, comprising:
   depositing a first copper powder layer across a substrate;
   subsequently selectively fusing the first copper powder layer via a fusing instrument;
   depositing a second copper powder layer across the first copper powder layer;
   selectively fusing the second copper powder layer via the fusing instrument; and
   depositing a plurality of additional copper powder layers wherein each additional layer is deposited on the previous layer;
   selectively fusing each of the additional copper powder layers; and
   creating a predetermined wick structure based on the selective fusing of each additional copper powder layer, wherein the predetermined wick structure is a multi-layer wick structure including a wick base layer, a liquid feeding post, and a wick cap layer, the predetermined wick structure being formed by a plurality of wick unit cells, each of the wick unit cells including an arched liquid feeding post, a structure based wick with non-uniform height that is thicker further from the arched liquid feeding post, and a tapered outlet vent, a top end of the arched liquid feeding post being thicker than a bottom end of the arched liquid feeding post.

2. The method of claim 1, wherein each copper powder layer is deposited via a print nozzle.

3. The method of claim 2, wherein the print nozzle is pre-programmed to create the predetermined multi-layer wick structure.

4. The method of claim 1, further comprising:
   removing loose copper powder remaining after selectively fusing each copper powder layer.

5. The method of claim 4, further comprising:
   replacing the removed loose copper powder with sacrificial carbonate particles, wherein the sacrificial carbonate particles include a binding agent that is curable between each layer, the sacrificial carbonate particles being removed when the additive selective laser sintering of the predetermined wick structure is complete.

6. The method of claim 1, wherein the copper powder is suspended in a slurry with a binding agent.

7. The method of claim 1, wherein the predetermined wick structure includes surface enhancement features, wherein the surface enhancement features include enhancements to the wick base layer or enhancements to the wick base layer and the substrate.

8. The method of claim 1, wherein the predetermined wick structure includes tilted liquid supply posts.

9. The method of claim 1, wherein the predetermined wick structure includes a manifold microchannel wick structure.

* * * * *